US005617157A

United States Patent [19]

Shalon et al.

[11] Patent Number: 5,617,157

[45] Date of Patent: Apr. 1, 1997

[54] COMPUTER CONTROLLED SUBJECTIVE REFRACTOR

[75] Inventors: Tadmor Shalon, Brentwood; Marvin L. Pund, Chesterfield; Susan L. Bragg, University City; James D. Houseman, Lake Saint Louis; Steven W. Free, Bridgeton, all of Mo.

[73] Assignee: Metaphase Ophthalmic Corp., St. Louis, Mo.

[21] Appl. No.: 260,027

[22] Filed: Jun. 15, 1994

[51] Int. Cl.[6] .......... A61B 3/02

[52] U.S. Cl. .......... 351/222; 351/233; 351/237; 351/244

[58] Field of Search .......... 351/200, 222, 351/236, 237, 239, 205, 211, 244, 245, 233

[56] References Cited

U.S. PATENT DOCUMENTS

| | | | |
|---|---|---|---|
| 3,487,069 | 12/1969 | Maselli | 351/211 |
| 3,536,383 | 10/1970 | Cornsweet et al. | 351/211 |
| 3,572,909 | 3/1971 | VanPatten et al. | 351/211 |
| 3,634,003 | 1/1972 | Guyton | 351/211 |
| 3,664,631 | 5/1972 | Guyton | 351/211 |
| 3,669,530 | 6/1972 | Guyton | 351/211 |
| 3,791,719 | 2/1974 | Kratzer et al. | 351/211 |
| 3,819,256 | 6/1974 | Bellows et al. | 351/211 |
| 3,879,113 | 4/1975 | Howland et al. | 351/211 |
| 3,883,223 | 5/1975 | Hudson | 351/211 |

(List continued on next page.)

OTHER PUBLICATIONS

Brochure entitled "Auto Kerato–Refractometer Kr–3000", Topcon, 104.

Brochure entitled "Auto Ref–Keratometer RK–2", Canon, 1–6.

Brochure entitled "TRS–1200 Total Refraction System" Marco Technologies, 1–4.

Brochure entitled "AR–1200 Automatic Refractor", Marco Technologies, 1.

Brochure entitled "ARK–2000 Automatic Refractor/Keratometer", Marco Technologies, 1–2.

*Duane's Clinical Opthalmology,* vol. 1, Chapter 67, entitled "Automated Clinical Refraction" by David L. Guyton, Revised Edition, 1992.

1994 edition of IC Master, vol. 1, pp. 2, 3, 726, 727.

Programmer's Guide to the EGA/VGA, Sutty and Blair, 1988, p. 10.

GE Owner's Manual, VHS Video Camera/Recorder, 1987, (3 pages).

Sony Corporation, Multiscan Operating Instructions, 1986, pp. 2, 3.

*Primary Examiner*—Huy Mai

*Attorney, Agent, or Firm*—Howell & Haferkamp, L.C.

[57] ABSTRACT

A computer controlled subjective refractor includes a microcomputer based remote hand control connected to an enclosure which houses the optical elements of the refractor and which controls their operation for the examination of a patient. The enclosure has a beam splitter extending at its bottom and a forehead rest extending near its bottom such that a patient's eyes are positioned near the bottom of the enclosure to view into the beam splitter and thereby materially reduce accommodation which would otherwise interfere with the accurate refracting of the patient's eyes. Movement and position location of the optical elements are achieved through a microcomputer based electronic controller which is in communication with the microcomputer remote hand control. Additionally, a microcomputer based target projector assembly may be used to selectively project any of a wide number of images comprised of eye charts and the like for testing the patient's vision. The subjective refractor thereby provides a network of microcomputer based electronic controls for very accurately positioning a plurality of optical elements and determining their position in order to determine the refractive correction of a patient's eyes. The handheld remote control includes an optical display and a number of finger controls through which an operator may actively interact with the subjective refractor as the patient is examined.

21 Claims, 15 Drawing Sheets

U.S. PATENT DOCUMENTS

| | | | |
|---|---|---|---|
| 3,883,233 | 5/1975 | Guilino | 351/211 |
| 4,021,102 | 5/1977 | Iizuka | 351/211 |
| 4,162,828 | 7/1979 | Trachtman | 351/211 |
| 4,180,323 | 12/1979 | Persson et al. | 351/211 |
| 4,239,351 | 12/1980 | Williams et al. | 351/211 |
| 4,253,743 | 3/1981 | Matsumura | 351/211 |
| 4,266,862 | 5/1981 | Trötscher et al. | 351/211 |
| 4,293,198 | 10/1981 | Kohayakawa et al. | 351/211 |
| 4,293,199 | 10/1981 | Wada et al. | 351/211 |
| 4,304,468 | 12/1981 | Wada | 351/211 |
| 4,353,625 | 10/1982 | Nohda et al. | 351/211 |
| 4,367,019 | 1/1983 | Kitao et al. | 351/211 |
| 4,372,655 | 2/1983 | Matsumura et al. | 351/206 |
| 4,373,787 | 2/1983 | Crane et al. | 351/210 |
| 4,390,255 | 6/1983 | Nohda et al. | 351/212 |
| 4,395,097 | 7/1983 | Mohrman | 351/201 |
| 4,396,258 | 8/1983 | Hazard | 351/243 |
| 4,407,571 | 10/1983 | Augusto | 351/237 |
| 4,410,243 | 10/1983 | Fürste | 351/211 |
| 4,421,391 | 12/1983 | Matsumura et al. | 351/211 |
| 4,444,476 | 4/1984 | Simon et al. | 351/211 |
| 4,453,808 | 6/1984 | Takahashi et al. | 351/208 |
| 4,529,280 | 7/1985 | Nohda | 351/211 |
| 4,531,526 | 7/1985 | Genest | 128/630 |
| 4,533,221 | 8/1985 | Trachtman | 351/203 |
| 4,637,700 | 1/1987 | Krueger | 351/211 |
| 4,640,596 | 2/1987 | Humphrey | 351/211 |
| 4,660,945 | 4/1987 | Trachtman | 351/203 |
| 4,697,895 | 10/1987 | Sekiguchi et al. | 351/243 |
| 4,707,090 | 11/1987 | Humphrey | 351/211 |
| 4,730,917 | 3/1988 | Kreuger | 351/211 |
| 4,740,071 | 4/1988 | Kobayashi | 351/206 |
| 4,753,527 | 6/1988 | Ishihara | 351/244 |
| 4,761,070 | 8/1988 | Fukuma | 351/205 |
| 4,772,114 | 9/1988 | Fukui et al. | 351/211 |
| 4,796,989 | 1/1989 | Fukuma et al. | 351/212 |
| 4,810,083 | 3/1989 | Okada et al. | 351/205 |
| 4,820,037 | 4/1989 | Kohayakawa et al. | 351/211 |
| 4,828,381 | 5/1989 | Shindo | 351/211 |
| 4,834,528 | 5/1989 | Howland et al. | 351/211 |
| 4,848,895 | 7/1989 | Kato et al. | 351/211 |
| 4,848,896 | 7/1989 | Matsumoto | 351/211 |
| 4,859,051 | 8/1989 | Fukuma et al. | 351/211 |
| 4,878,750 | 11/1989 | Sekiguchi | 351/212 |
| 4,917,480 | 4/1990 | Kato et al. | 351/211 |
| 4,952,049 | 8/1990 | Matsumoto | 351/211 |
| 5,010,893 | 4/1991 | Sholder | 128/782 |
| 5,011,276 | 4/1991 | Iwamoto | 351/211 |
| 5,026,151 | 6/1991 | Waltuck et al. | 351/246 |
| 5,042,940 | 8/1991 | Iwamoto | 351/208 |
| 5,121,981 | 6/1992 | Waltuck et al. | 351/243 |
| 5,157,427 | 10/1992 | Humphrey | 351/205 |
| 5,208,619 | 5/1993 | Campbell | 351/211 |
| 5,210,555 | 5/1993 | Ishikura et al. | 351/211 |
| 5,249,003 | 9/1993 | Kohayakawa | 351/211 |

COMPUTER CONTROLLED SUBJECTIVE REFRACTOR

BACKGROUND AND SUMMARY OF THE INVENTION

There are many instruments in the prior art directed to determining the refractive correction of a patient's eyes. With the advent of computers, instruments have become commercially available which utilize computers in an attempt to automate what was previously a manual operation. However, almost all of these instruments suffer from the problem of instrument accommodation which may significantly impact the measured correction. This phenomena relates to the patient's tendency to "accommodate" or unconsciously adjust their eyes as they bring their face close to an instrument. This results in squinting, straining, or otherwise forcing the eyes to adjust and focus near rather than the patient relaxing and letting the instrument "correct" for the eyes' deficiency at distance. While various techniques have been developed in an attempt to control accommodation, such as fogging one eye while refracting the other, by and large these have met with only limited success in automated instruments.

Adaptation of computers to these instruments has provided some advantages, such as providing digital outputs, electronic measurement of lens positions to provide greater accuracy, more sophisticated operator input and control over the testing process, etc. However, all of these supposed advantages have not been realized due to the inherent problem of accommodation which has not been solved. Furthermore, in such prior art devices as are known to the inventors herein, the needs of the user have not been addressed such that computer controlled devices have become more complex and difficult to operate than the prior art manual devices instead of easier and simpler. The concept of "user friendliness" has not been addressed so as to minimize the training required for an operator to effectively use a device to achieve an accurate measurement of a patient's refractive correction.

In order to solve these and other problems in the prior art, the inventors herein have succeeded in designing and developing a subjective refractor which is elegantly simple in design and which utilizes programmed microcomputer technology to simplify its operation such that users are logically guided through the examination process. Another significant advantage of the present invention is its approach in reducing the patient accommodation phenomenon. The instrument is conveniently mounted at the end of an arm, much as a prior art refractometer, except that it is positioned at the patient's forehead and extends upwardly therefrom. The only portion of the instrument which extends downwardly into the patient's line of sight is a beam splitter through which the patient may clearly view the far wall or any other background provided in the room. This "fools" the patient into believing that there is nothing close to his face or eyes and reduces the patient's tendency to subconsciously "adjust" his eyes. By dramatically reducing patient accommodation, the instrument's ability to accurately refract the eye has been greatly improved over those instruments in the prior art. Additional improvement in accuracy has been attained by utilizing separate microcomputers for controlling various parts of the instrument, with the microcomputers being in communication. An operator's remote control is hardwired to the instrument to permit an operator to move about the patient freely during the examination. The remote control unit includes a number of finger controls through which the operator may control the operation of the instrument during the examination, and has a display to indicate to the operator the eye target being displayed to the patient as well as the refractive correction indicated by the instrument, all on a real time basis. An operator may watch the patient's eyes adjust during the examination which provides a direct indication to the operator of the patient's response.

Still another feature of the present invention is a computer controlled electronic target projection assembly which permits an operator to selectively project any one of a series of pre-programmed eye charts, or any other customized eye chart, for patient viewing in the far vision mode. This target projection assembly is conveniently mounted internal to the instrument and eliminates the use of eye charts positioned at inconveniently long distances from the patient. Furthermore, the ability of an operator to switch from one eye chart to another permits him to adjust for a patient's "learning" the chart and to otherwise provide interest to the patient during the examination, thereby further distracting him from the process and minimizing accommodation. This feature also provides for extending the functionality of the present invention to permit patient testing for information regarding neurological and physiological diseases of the eye which are not generally considered to be characteristic of refraction. These tests are conveniently formed within the enclosed refractor system of the present invention which allows a better control of the environmental conditions in which the patient is being tested. One example of these other tests includes a type of response test administered by varying the contrast present in any one of the pre-programmed eye charts. This test measures the patient's detection of the contrast ratio between the brightness of the chart items and the brightness of the background that the items are displayed upon. Secondly, a glare test can be performed by shining one or more bright lights into the patient's eyes while the patient is viewing a chart. Patients with cataracts or other media opacities will see streaks and glares of light which "wash out" the chart. A patient's subjective responses may be solicited to quantify the amount of visual degradation. This increased functionality of the present invention extends it from being considered solely as a refractometer into a more generalized vision platform.

The instrument also includes another microcomputer for controlling the movement of various optical elements contained within the assembly. These movable optical elements include those which are moved to adjust the refraction of the instrument, their position thereby being indicative of the refractive correction, as well as those optical elements which must be moved to change the patient's line of sight from a near vision to a far vision path, or vice versa. While the instrument is binocular, the microcomputer may also occlude one eye or the other for monocular measurement, or for other purposes as known in the art. For measuring near vision, a reading card is manually positioned by an operator and its distance is measured and input to the computer by an encoded distance measuring device which extends outwardly from the back of the instrument.

As mentioned, the three microcomputers are electronically linked and are in communication under a master-slave relationship providing operator control through the handheld remote control. Thus, with the present invention, microcomputers have been adapted to the instrumentation to simplify it instead of making it more complex. Furthermore, microcomputers provide digital input and output which allows communication with other computers in the doctor's office to automatically record the measured patient's refractive correction and store it without recopying onto a patient's card or the like which may result in error. These microcomputers not only provide more accurate measurement, but the inventors' approach of locating the optical and electronic assemblies in an enclosure which is positioned at eyebrow level and above dramatically decreases patient accommodation such that this increased accuracy is not "lost" in the distortion caused by patient accommodation. It is believed that the present invention will provide dramatic improvement in the quality of optical services provided for these reasons.

While the principal advantages and features of the present invention have been described above, a more complete and thorough understanding of the invention may be attained by referring to the drawings and description of the preferred embodiment which follow.

DETAILED DESCRIPTION OF THE PREFERRED EMBODIMENT

Before providing a detailed description of the various components of the present invention, it may be helpful to briefly describe the instrument in summary fashion. Generally, the subjective refractor of the present invention includes a main enclosure containing opto-mechanical elements that are moved by motors, elements that are moved manually, and elements that remain static. There are two major motor driven opto-mechanical assemblies that provide the variable optical power of the refractor: the trombone assembly which linearly translates mirrors M1 and M2 to provide variable spherical power; and the cylinder assembly which both translates and rotates lenses L5 and L6 to provide both variable cylinder power and axis (see FIG. 1). Other motor driven assemblies are included to move optical elements in and out of the optical path (like the occluder), and to adjust the inter-pupillary spacing. A manually controlled element (which could be readily motorized) and a motor controlled element allow the refractor to be toggled between far vision and near vision patient sight paths and also to correctly position the patient with respect to the instrument. A number of static optical mounts maintain the position and alignment of the fixed optical elements and serve as the platform for mounting the moveable elements.

Figure 1:
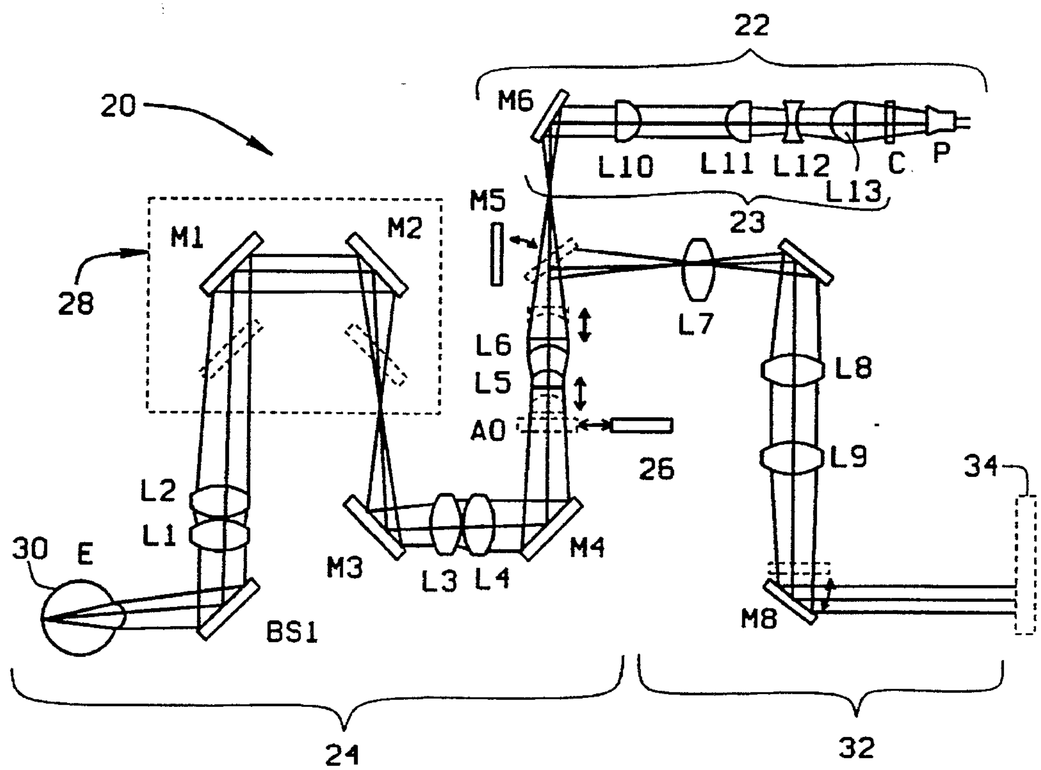
FIG. 1 is a schematic diagram of the optical elements included in the present invention.

Referring to FIG. 1, the subjective refractor 20 shown is comprised of a plurality of optical elements which may be conveniently moved for testing a patient's visual acuity when the patient is viewing either a very distant object and the patient is not accommodating, or a closely placed object. Only one side (for the left eye) of a fully binocular system is shown in FIG. 1. All of the adjustable optical elements included as part of FIG. 1 are also present in a mirror image for the other eye and perform the same optical functions as described for those as shown in FIG. 1. Both eyes share the optics of the common chart projector assembly (described below) as the light from the illuminator source is divided into two paths by a beam splitter that is located in the collimated section of the projector optics.

Referring now more specifically to the elements shown in FIG. 1, the target projector assembly 22 includes a projector lamp P shining light through a liquid crystal display (LCD) chart image C and a field lens L13. The light then travels through lenses L12–L10 and reflects off mirror M6 to enter the optics common to the far and near paths of the left eye side shown in FIG. 1. Mirror M5 moves in and out of the optical path to switch between the near and far vision paths. The mechanical mechanism for moving mirror M5 is described in greater detail below. When M5 is out of the path, light is able to travel from the target projector assembly 22 into the shared vision path optical elements 24. Light from the target projector assembly 22 is incident upon a moveable pair of lenses L5 and L6 which control the variable cylindrical power of the subjective refractor 20. The distance between the lenses changes the power of the focusing light. The rotation of the L5 and L6 lens pair about the optical axis controls the axis of the cylindrical power. After the L5 and L6 lens pair is an aperture A0 which contains interchangeable optics 26. For example, this port can be supplied with a prism for beam deviation, an occluder to obstruct the beam (for monocular operation), or a clear aperture so the beam remains unaffected. Still another example for optics 26 is a variable prism pair which can be rotated relative to one another to provide a large prism diopter range, including a zero prism diopter deviation. This permits measurement of phorias which are deviations of the eye away from the optical axis of the object being viewed. After aperture A0, the light reflects off mirror M4 and travels through the lens pair L3–L4 onto mirror M3 and into the trombone assembly 28. Mirrors M1 and M2 comprise the optical elements included in this trombone assembly 28 and they are moved in synchronism to provide the variable spherical power of the system by changing the path length between lens pairs L3–L4 and L1–L2. The remainder of the common optics 24 are stationary and consist of the lens pair L1–L2 and the beam splitter BS1. Light reflected off beam splitter BS1 impinges on the patient's left eye and is sharply focused onto the retina when the subjective refractor 20 has been adjusted to compensate for the refractive errors present in the eye 30.

Figure 15:
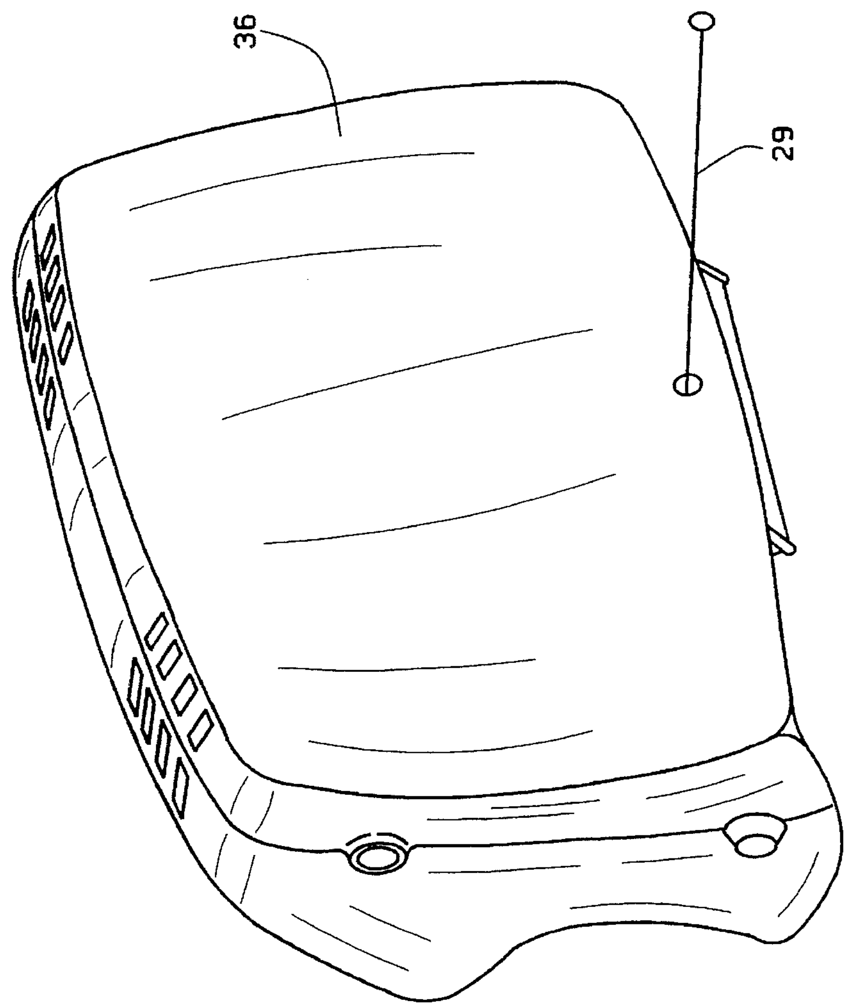
FIG. 15 is a back view of the enclosure detailing the Prince rule for measuring the near vision working distance.

The near vision optical elements 32 share the common vision path optical elements 24 when mirror M5 is moved into its dotted line position as indicated in FIG. 1, i.e. in the light beam path. When so positioned, light reflected from object 34 reflects off mirror M8, through lenses L9 and L8, off mirror M7, through lens L7, and off mirror M5 to join the common vision path optical elements 24. Typically, object 34 may be a near vision reading card or other eye chart as known in the art for detecting near vision correction. A Prince rule, such as a wire type distance encoder 29 as shown in FIG. 15 may be used to electronically encode the distance between object 34 and the patient's eyes. When mirror M8 is not being used for near vision refraction, it is flipped up into its dotted line position as shown in FIG. 1 to clear the patient's view to his surroundings. Thus, a patient's eye 30 may conveniently see through beam splitter BS1 and beyond to the far wall or other physical objects as the patient's line of sight is unobstructed. During far vision refraction, the target projector assembly 22 projects its target which is apparently displayed to the patient via beam splitter BS1 such that it appears to be "projected" at infinity against the far wall of the room in which the patient is positioned.

Figure 2:
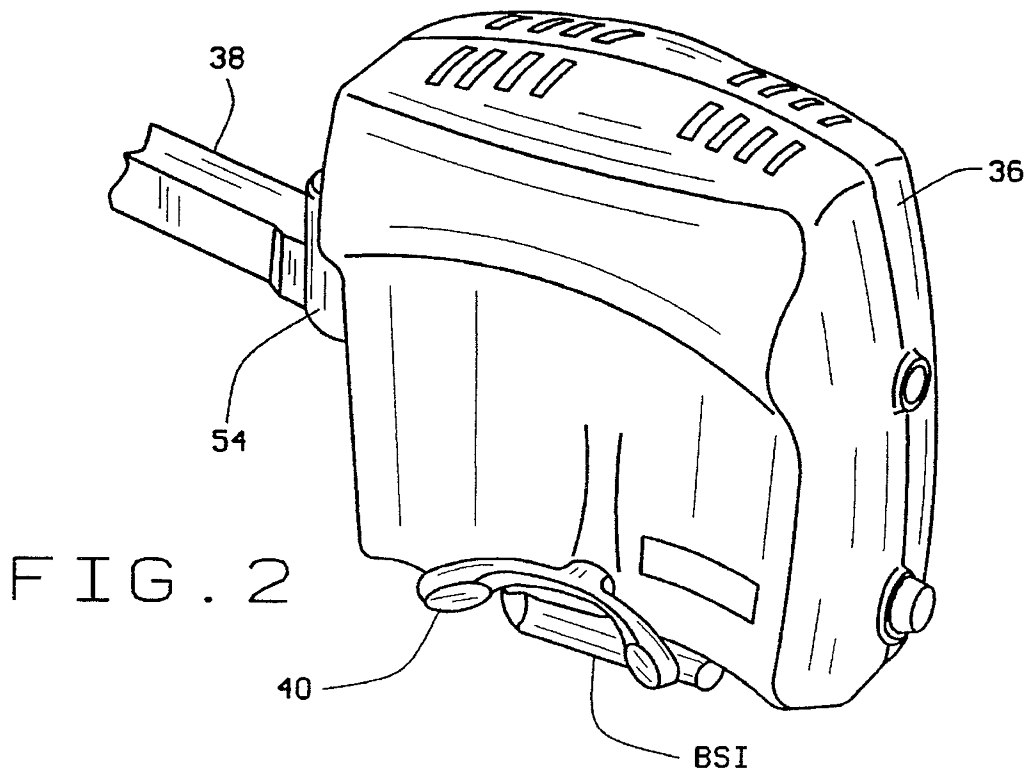
FIG. 2 is an isometric view of the arm mounted enclosure which contains the electronics and optics of the present invention.

As shown in FIG. 2, beam splitter BS1 is mounted to and extends downwardly from the enclosure 36 within which the subjective refractor 20 is mounted on an arm 38 for movement and adjustment about the patient's face. A forehead rest 40 is pivotally mounted to the lower portion of the front side of the enclosure 36 and provides a convenient physical positioning of the patient's forehead during an examination. With this orientation, it may be readily understood that the enclosure 36 extends from a point above the patient's eyes upwardly such that the patient's eyes are aligned with the beam splitter BS1 to look out into the room beneath enclosure 36. This greatly reduces any patient accommodation by giving the patient a feeling of open space and reducing the tendency for a patient to feel that his face is near or adjacent any other object.

Having provided an overview of the optics and general arrangement of the subjective refractor 20, a more detailed description of the various mechanical and electronic assemblies comprising the subjective refractor 20 will now be explained.

Basic Refractor Assembly

Figure 3:
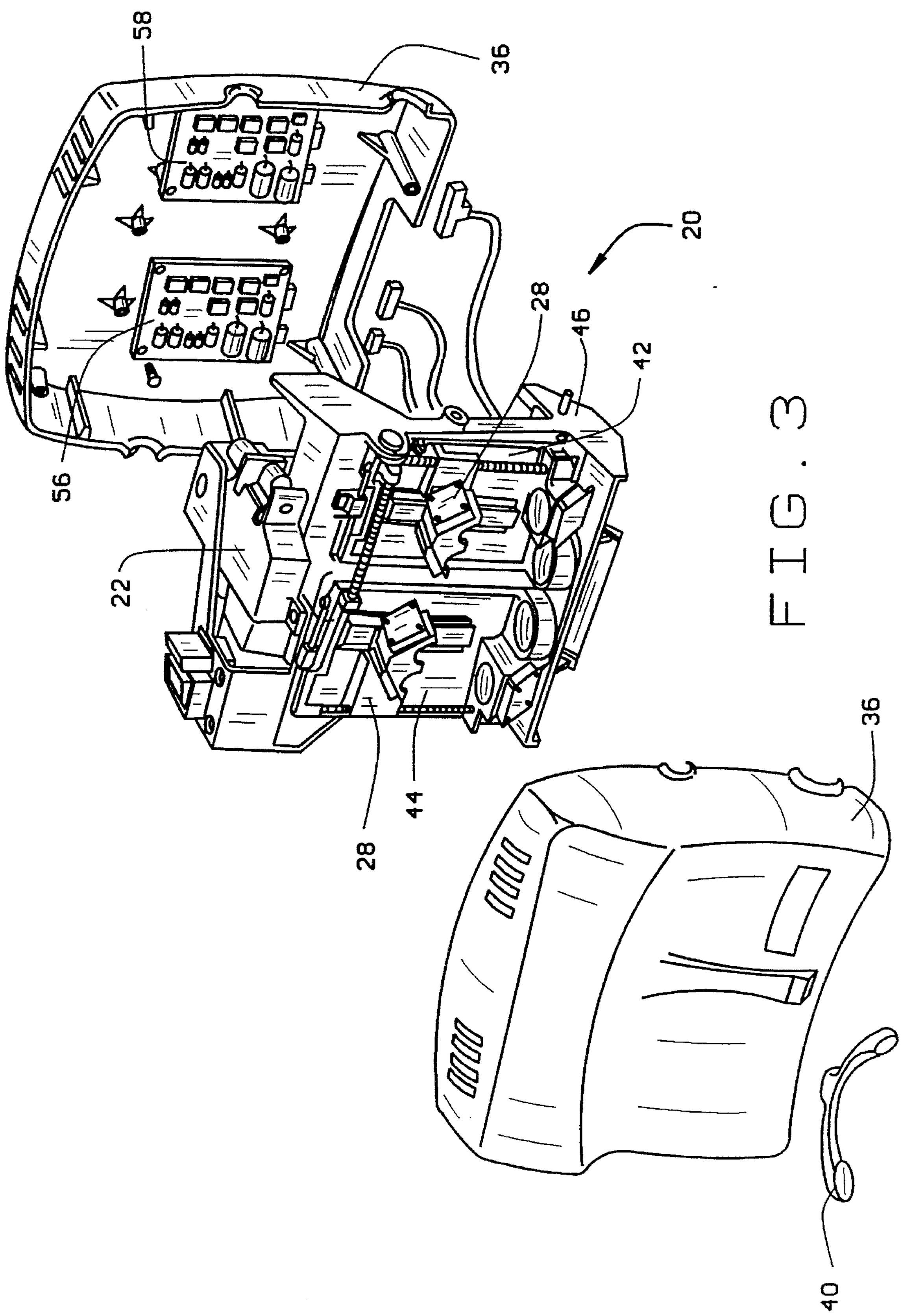
FIG. 3 is a final assembly drawing providing further detail of the interior of the enclosure.
Figure 4:
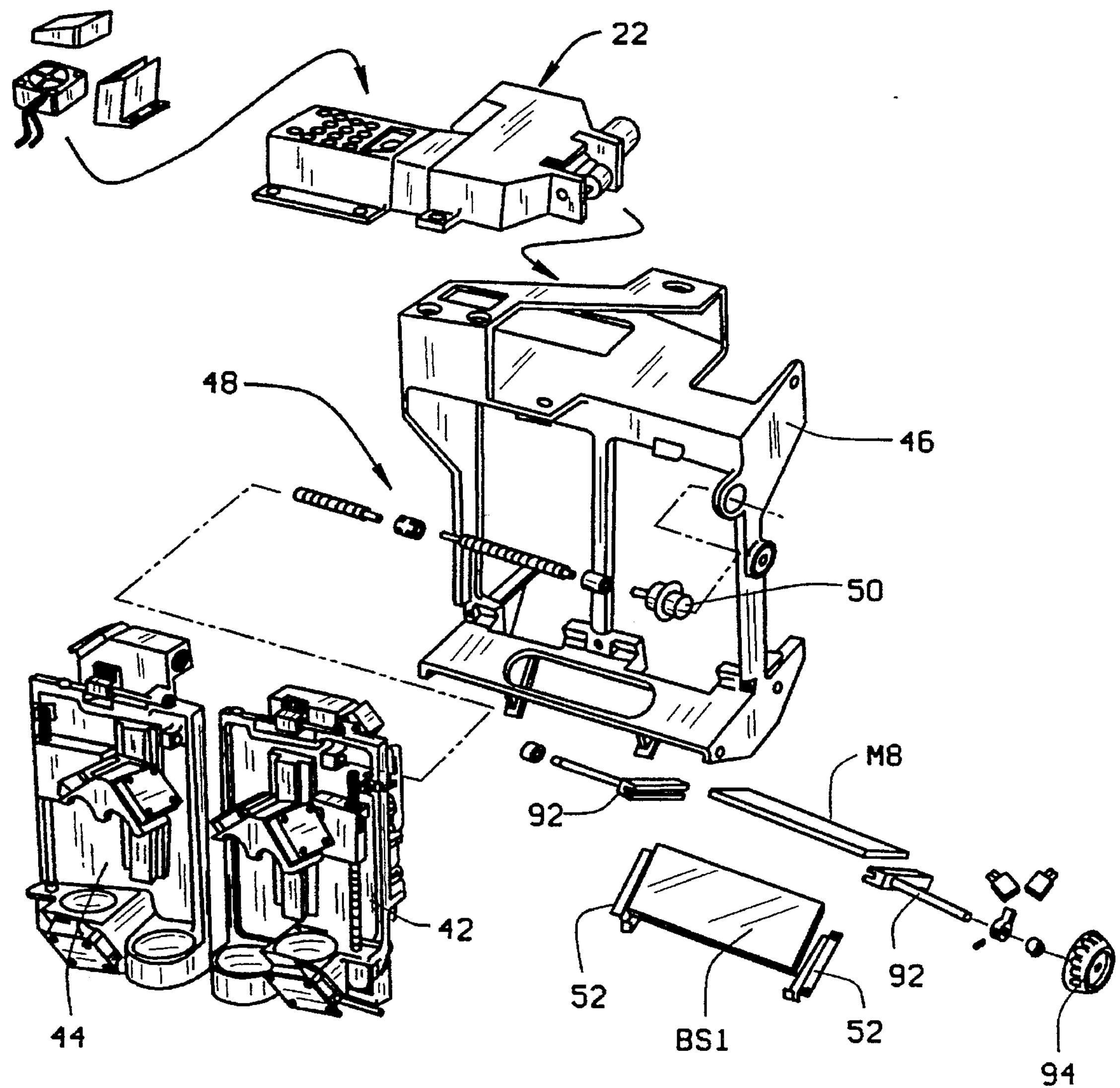
FIG. 4 is an assembly drawing further detailing the mechanical arrangement of the optics.

The subjective refractor 20 (see FIG. 3) includes a pair of base plates 42, 44, one for the right eye opto-mechanics and the other for the left eye opto-mechanics. Optical elements and moving assemblies of the subjective refractor 20 are mounted on both sides of each base plate 42, 44. The base plates 42, 44 are moveable to the left and right about the refractor center (approximately the location of the patient's nose) to adjust for the variable inter-pupillary spacing encountered in the patient population, as is more fully explained below. Briefly however, as shown in FIG. 4, base plates 42, 44 are mounted to a framework 46 with a threaded shaft assembly 48 driven by a motor 50 for remote adjustment thereof by an operator prior to examination. The target projector assembly 22 is mounted to framework 46, and framework 46 is mounted to enclosure 36, as shown in FIG. 3. With this mounting arrangement, the target projector assembly 22 is mounted independently of the base plates 42, 44 such that their adjustment does not alter the projected target. The output from the target projector assembly 22 is split in a collimated optical space and directed into the optics of each base plate 42, 44 at any inter-pupillary distance.

Figure 5:
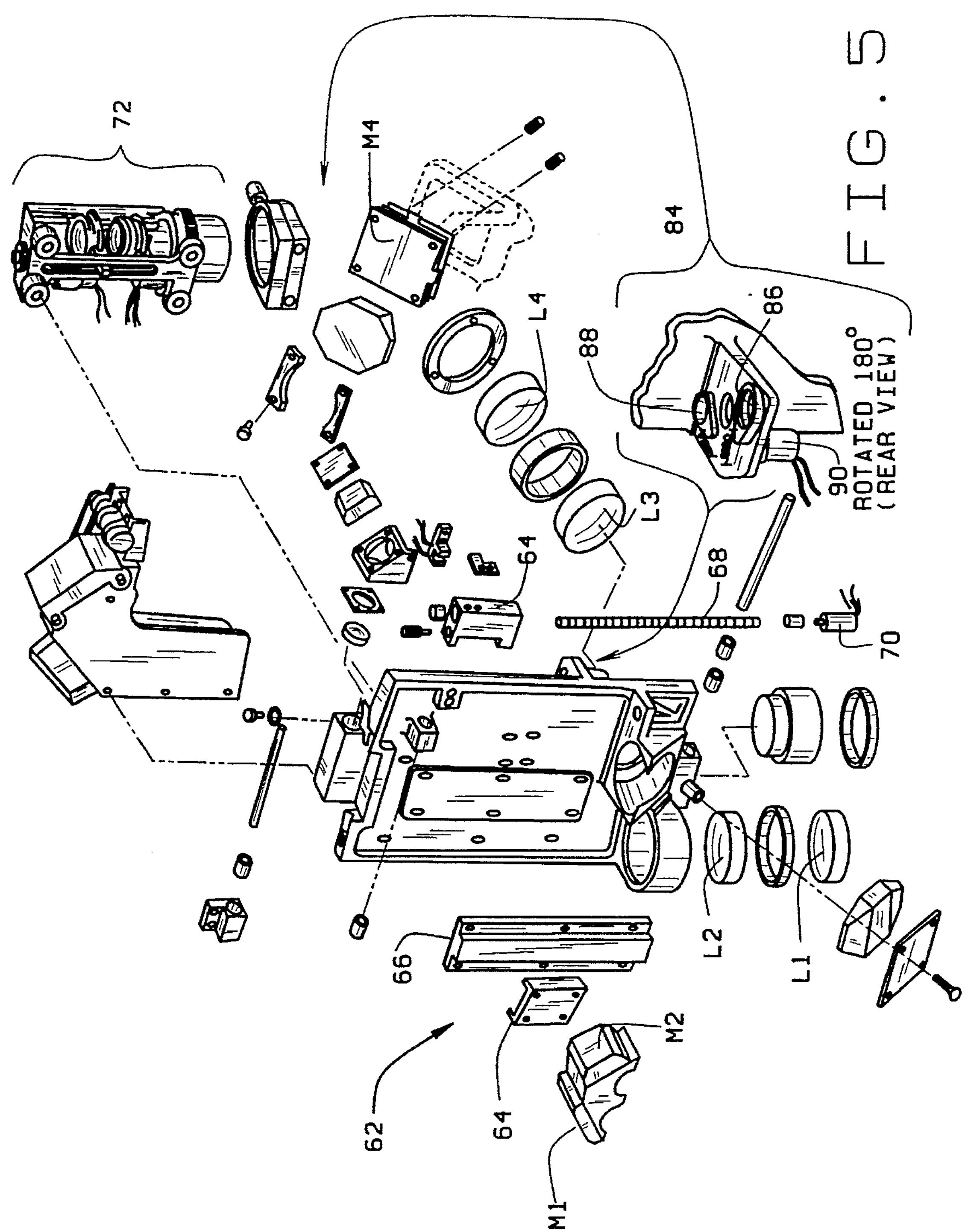
FIG. 5 is an exploded view of the various components comprising the base plate assembly.

As shown in FIG. 4, the same beam splitter BS1 is also shared by base plates 42, 44 and is permanently mounted at a 45° angle relative to the base of enclosure 36 by a pair of brackets 52. The forehead rest 40 is adjustable with respect to enclosure 36 to permit an operator to control the distance from the patient's corneal surface to the subjective refractor 20. Most appropriately, this adjustment will position the patient's corneal surface at the vertex distance expected in a pair of spectacles, i.e. the distance from the cornea to the back surface of the spectacle lenses. Adjustment guides may be provided to assist the operator in correctly positioning the patient's eye. As shown in FIG. 2, a mount 54 for mounting the subjective refractor 20 to arm 38 provides both tilt and rotation adjustment to provide a comfortable patient position in the refractor forehead rest 40. A pair of PC boards 56, 58 may conveniently mount the electronics for the subjective refractor 20 (and another ancillary device), except those which are provided in the remote control 60 (see FIG. 8). The trombone assembly 28 (see FIGS. 3 and 5) provides the simultaneous mechanical displacement of mirrors M1 and M2 required to introduce variable spherical power in the subjective refractor 20. Trombone assemblies 28 are located on both base plates 42, 44, allowing independent adjustment for the right and left eyes. As shown in FIG. 5, mirrors M1 and M2 are permanently oriented with respect to each other to provide a fixed 180° beam turning in the optical path between the fixed lens elements L1–L2 and L3–L4. By varying the path length between the fixed lens elements L1–L2 and L3–L4, the spherical power of the system is changed. The mirrors M1 and M2 are mounted on a precision machined bracket 63 which holds the mirror front surfaces at a constant 90° with respect to each other. The bracket 63 is in turn precision mounted on a carriage 64 which is driven on a linear ball bearing slide 66 by a threaded shaft 68 driven by a miniature DC servo motor 70. Magnetic encoder feedback is provided to reproducibly acquire and maintain a commanded position for the microcomputer which controls the movement of mirrors M1 and M2 (see the Electronics Section).

Cylinder Assembly

Figure 6:
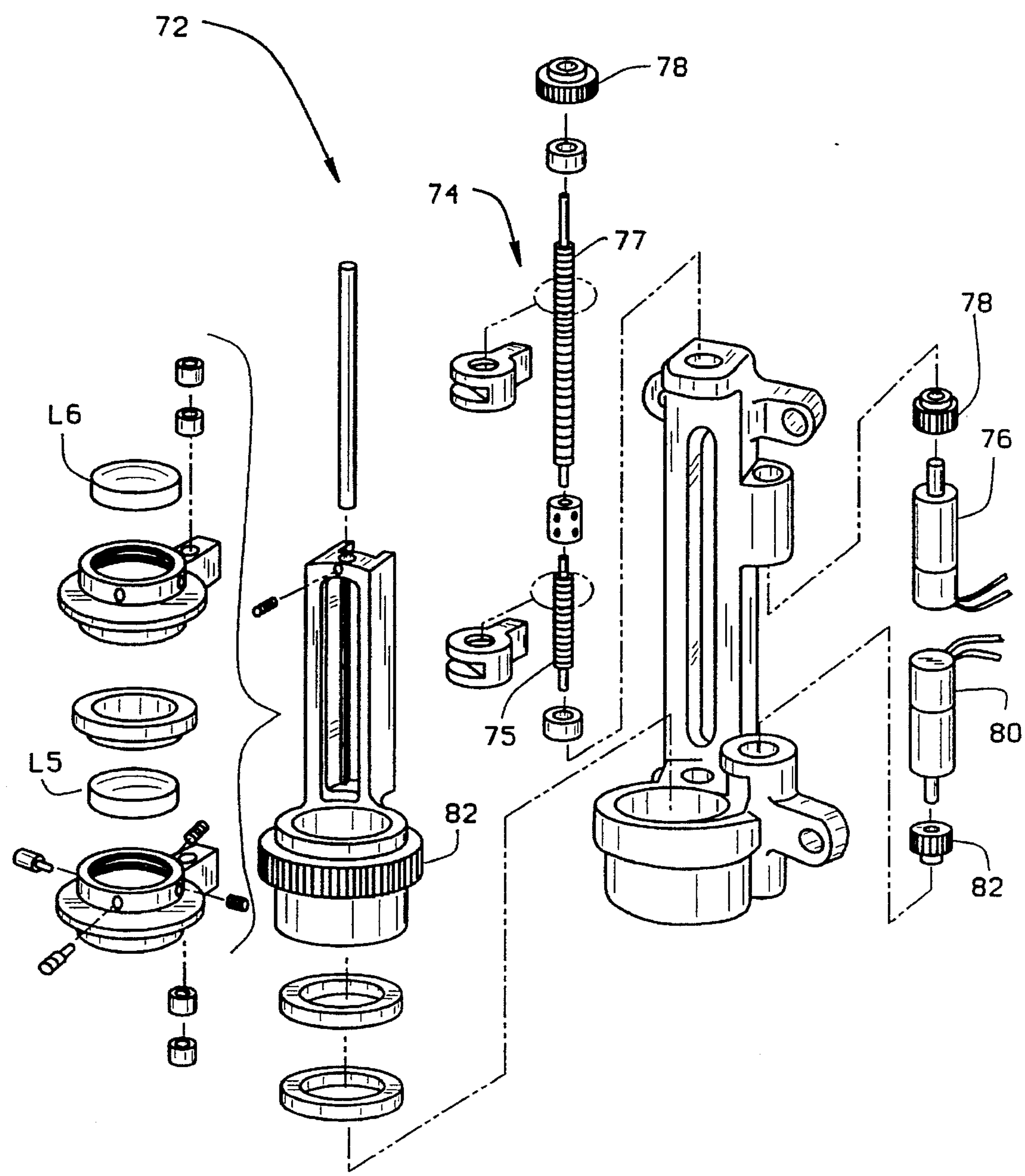
FIG. 6 is an exploded view of the cylinder assembly.

A cylinder assembly 72 (see FIG. 6) provides the mechanical motions of lenses L5 (a plano convex cylindrical lens producing plus cylinder power) and L6 (a plano concave lens producing negative cylinder power) required to produce both variable cylindrical power and variable cylinder axis. Two cylinder assemblies 72 are utilized, one mounted on the right base plate 42 and the other on the left base plate 44. This allows the completely independent setting of cylindrical power for each patient's eye. To produce varying cylindrical power, the lenses are linearly displaced relative to each other, i.e., the spacing between the lens centers is increased to increase the cylindrical power. At the null position of the cylinder lenses, when they nearly touch at the lens centers, the combination of L5 and L6 produces no power at all. As the lenses are driven apart from one another, the cylindrical power is increased. The lenses are moved in a 2:1 ratio, with lens L6 moving twice the distance of lens L5. The mechanical assembly simultaneously translates both lenses in carriers geared to a linear threaded drive assembly 74. The required 2:1 ratio is provided in threaded drive. The drive shafts 75, 77 are driven by a miniature DC motor 76 through a pair of gears 78. The cylinder assembly 72 also provides the required variable cylinder axis angle for the refractor 20. This is accomplished by jointly rotating the lens pair L5, L6 about their common optical center. The cylinder power axes of lenses L5 and L6 are precisely co-aligned during assembly. This common axis of power is then rotated to vary the axis angle observed by the patient. In the mechanical assembly, this is accomplished by rotating the entire linear threaded drive assembly 74. Thus, for any linear displacement of the lenses L5, L6, they may be rotated to any angle. It is sufficient that the lenses L5, L6 rotate through a 180° angle as the optical system is symmetric. This rotation is achieved by a DC motor 80 and gears 82.

Inter-pupillary Distance Assembly

The inter-pupillary distance (see FIG. 4) of the refractor 20 is adjustable by moving the two base plates 42, 44 apart or together relative to the refractor center line. The base plates 42, 44 are adjusted by the operator to bring the optical axis of each base plate 42, 44 into alignment with the patient's pupils, for example when the patient is focused at infinity. This allows the patient to binocularly view the eye chart. The two base plates 42, 44 are driven simultaneously from a single threaded shaft assembly 48 mounted to the framework 46 and driven by a stepper motor 50.

Prism-Occluder Assembly

The prism-occluder assembly 84 (see FIG. 5) is located at the aperture AO in FIG. 1. Although it is possible to mount a variety of optical elements at this position in the refractor 20, currently both a prism 86 to produce vertical dissociation and an occluder 88 are utilized. These elements 86 and 88 are rotated in and out of the optical path under computer control to produce the desired effect during testing. Both the prism 86 and the occluder 88 are directly driven by a DC motor 90. A prism-occluder assembly 84 is mounted on each base plate 42, 44 to provide independent testing of each eye.

Near Vision Optical Elements

The conversion of the subjective refractor 20 from far vision to near vision is achieved by moving both mirrors M5 and M8. Mirror M5 must be inserted in the optical path. Mirror M5 directs the patient's view through the remainder of the optical path, while mirror M8 deliberately blocks the patient's view through beam splitter BS1. The patient views the test object 34 and surrounding area through the near vision optics 32 of the subjective refractor 20.

Figure 7:
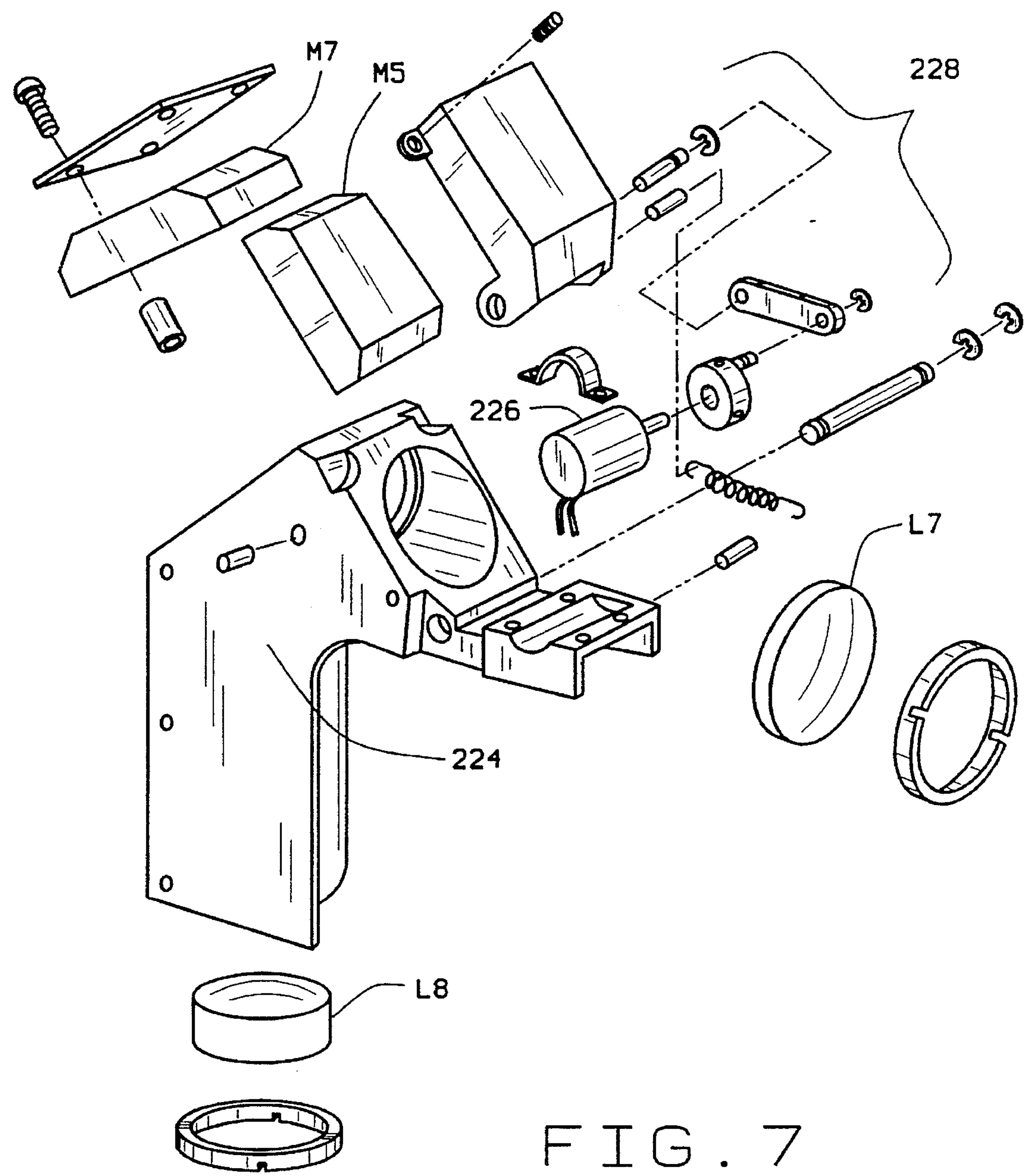
FIG. 7 is an exploded view of the near vision gate assembly.

As shown in FIG. 4, M8 is mounted by a pair of brackets 92' to framework 46 and has a finger knob 94' for moving M8 between a downward, near vision position and an upward, far vision position. As shown in FIG. 7, M5 is pivotally mounted to a support bracket assembly 224 and has a DC drive motor 226 which drives a lever arm linkage assembly 228 for moving M5 between a downward near vision path and an upward far vision path. As would be clear to those of ordinary skill in the art, mirror M8 could also be motor driven, or a mechanical linkage secured between mirrors M5 and M8 such that a single motor could drive them both between a near vision and far vision position. However, these details are considered to be design choice and the inventors are disclosing that which they consider to be their preferred embodiment at this time.

Operator's Remote Control

Figure 8:
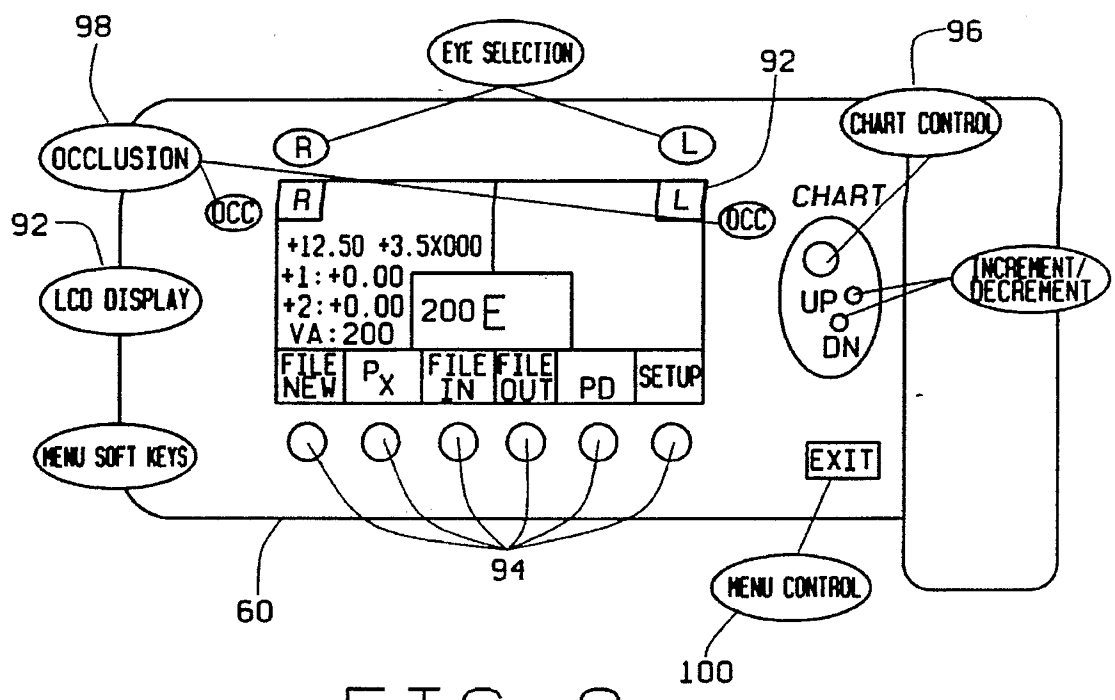
FIG. 8 is a plan view of the handheld remote control including display and control buttons.

The operator's remote control 60 is shown in FIG. 8 and is coupled with a hardwired connection to the electronics in enclosure 36. The remote control provides the interface for an operator with the subjective refractor 20 and permits feedback through information displayed on the display screen 92. As shown therein, the right side of the display 92 includes the refractive correction for the left eye (which is on the operator's right) and the left side of the display screen 92 includes the refractive correction for the right eye. Shown in the center portion of the display is a reproduction of the eye chart being shown to the patient. Along the lower portion of the display are a number of icons which correspond to the menu soft keys 94 as required for the operator to interact with the computer controlled remote control 60. A chart control 96 is provided along the right side of the remote control 60 along with increment/decrement buttons to enable an operator to "thumb" through the charts. An occlusion button 98 permits the operator to occlude rapidly either one of the right or left eyes, as desired for monocular examination. A menu control button 100 permits an operator to progress through the function menus. A complete and detailed description of operation for the handheld remote control 60 may be found in Exhibit B attached.

Electronics

Figure 9:
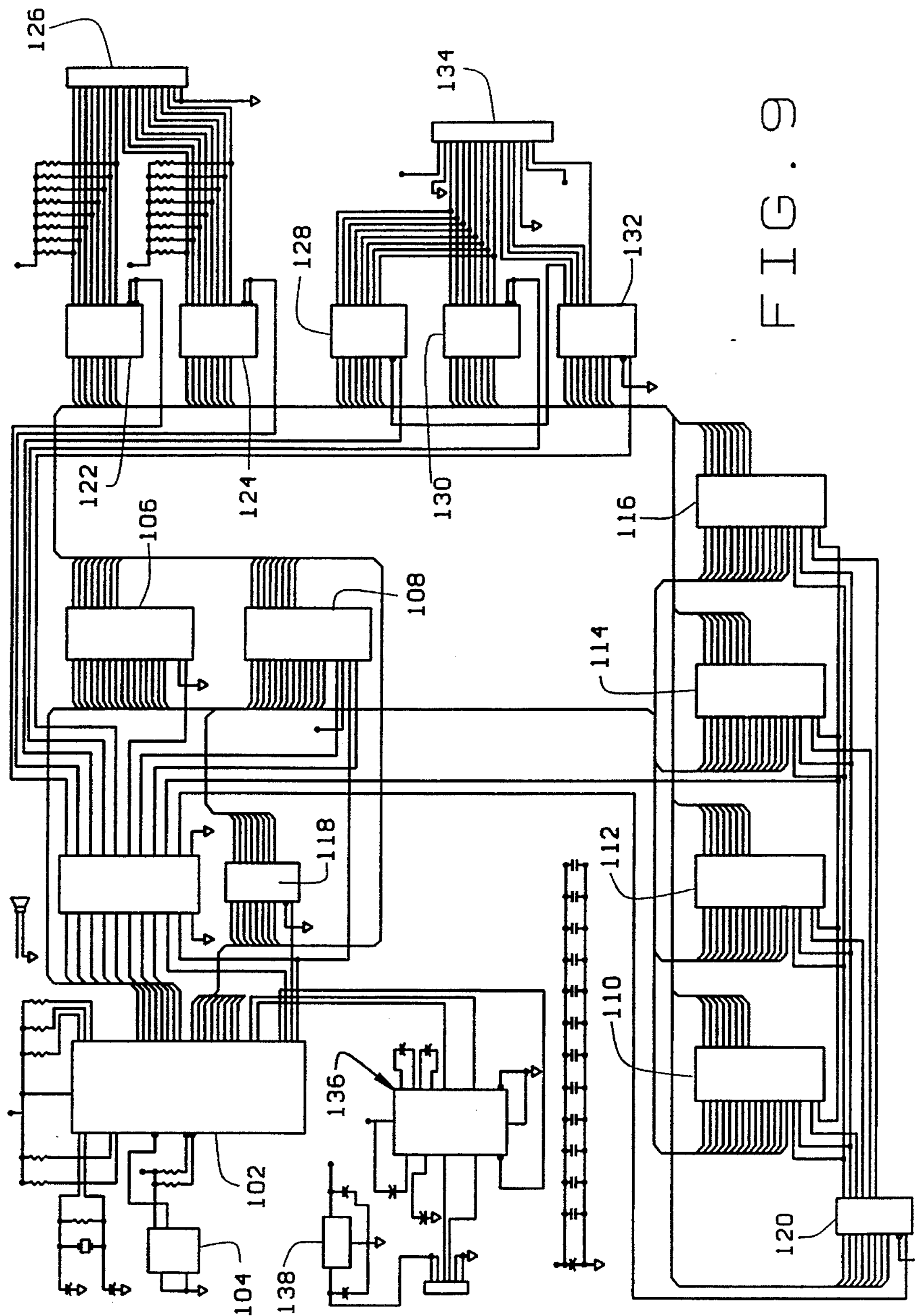
FIG. 9 is an electrical schematic of the microprocessor based handheld remote control.

As mentioned above, the handheld remote control 60 includes electronics which are shown in greater detail in FIG. 9. The operation of the handheld control 60 is centered in microprocessor 102 which may be a 68HC11E1 or equivalent, with a supervisory chip 104 to provide reset timing during power-on or low power supply situations. Microprocessor 102 utilizes a PROM memory 106, a RAM memory 108, and PROM memories 110–116, as required, for storing its control program, addressing information, operational data, etc. A latch register 118 performs capture of lower order address bits for extending the addressing capabilities of microprocessor 102, as is known in the art. Similarly, latch register 120 facilitates addressing the PROMs 110–116. Buffers 122 and 124 provide microprocessor access to the signals received from the finger controls 94 on remote control 60 as transmitted through a connector 126. Data register 128, data buffer 130, and control register 132 facilitate communication between microprocessor 102 and the LCD display 92 through connector 134. An RS232 driver circuit 136 facilitates communication between the microprocessor 102 and other microprocessors as described below such that microprocessor 102 permits an operator to control the subjective refractor 20 from the handheld control unit 60. Lastly, a voltage regulator circuit 138 regulates the voltage for the electronic circuit elements as shown in FIG. 9 and as are contained in the handheld control 60.

Motor Controller

Figure 10:
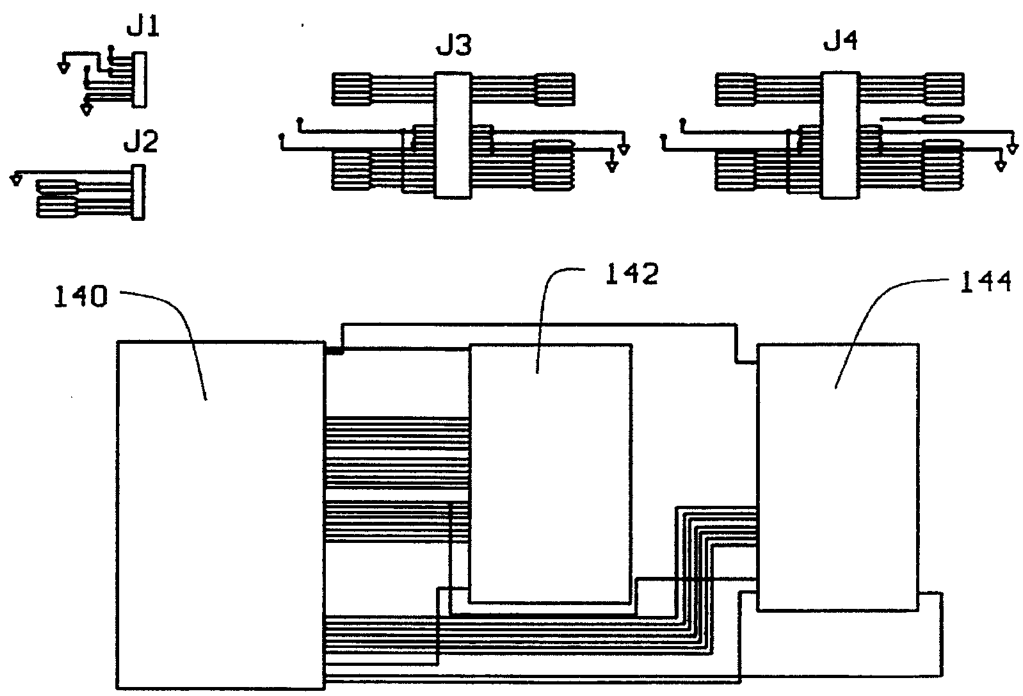
FIG. 10 is an electrical schematic/block diagram of the microprocessor based motor control unit.
Figure 10:
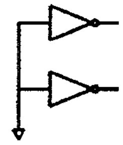
Figure 11:
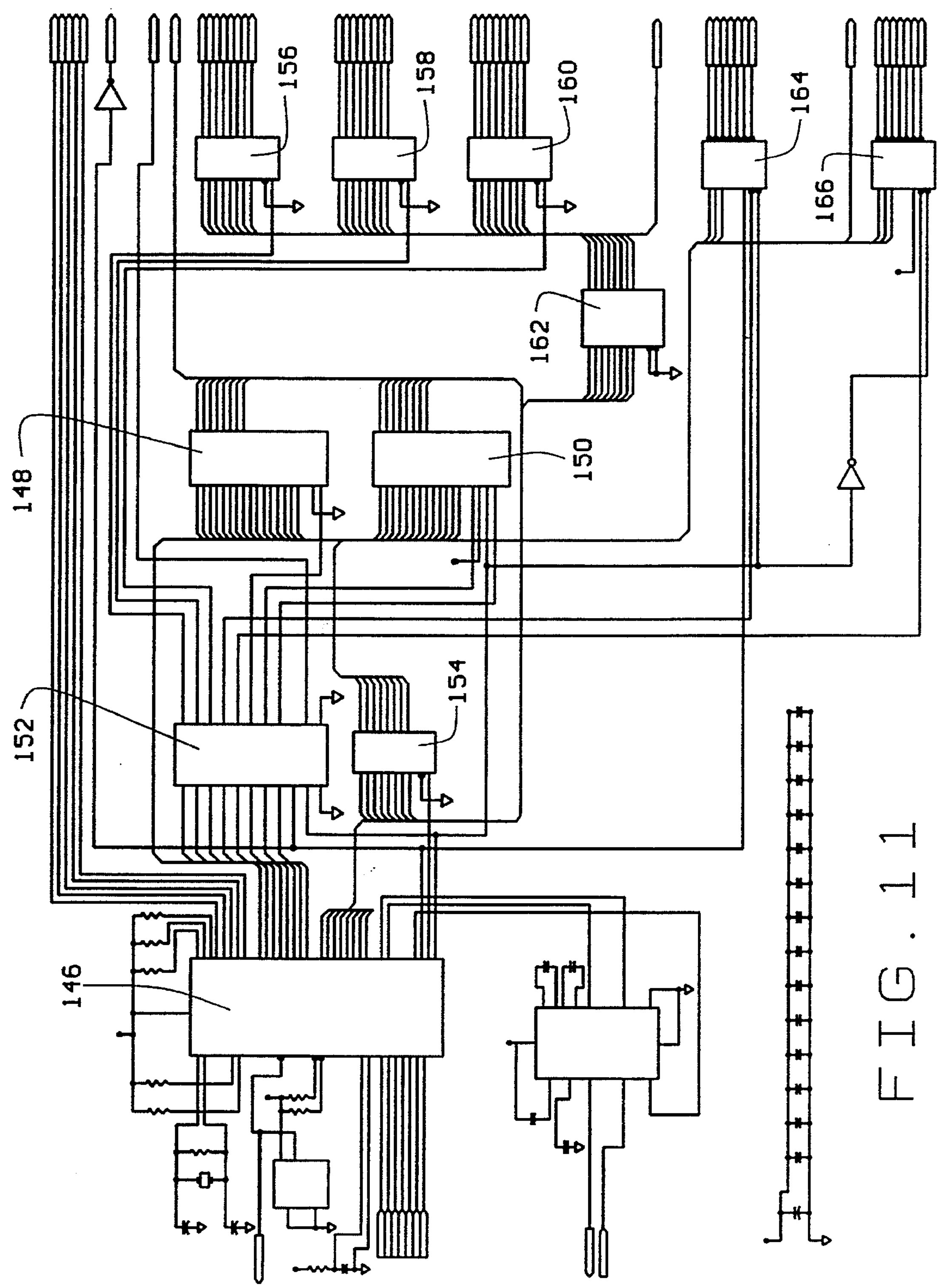
FIG. 11 is an electrical schematic of the microprocessor portion of the motor controller unit.
Figure 12:
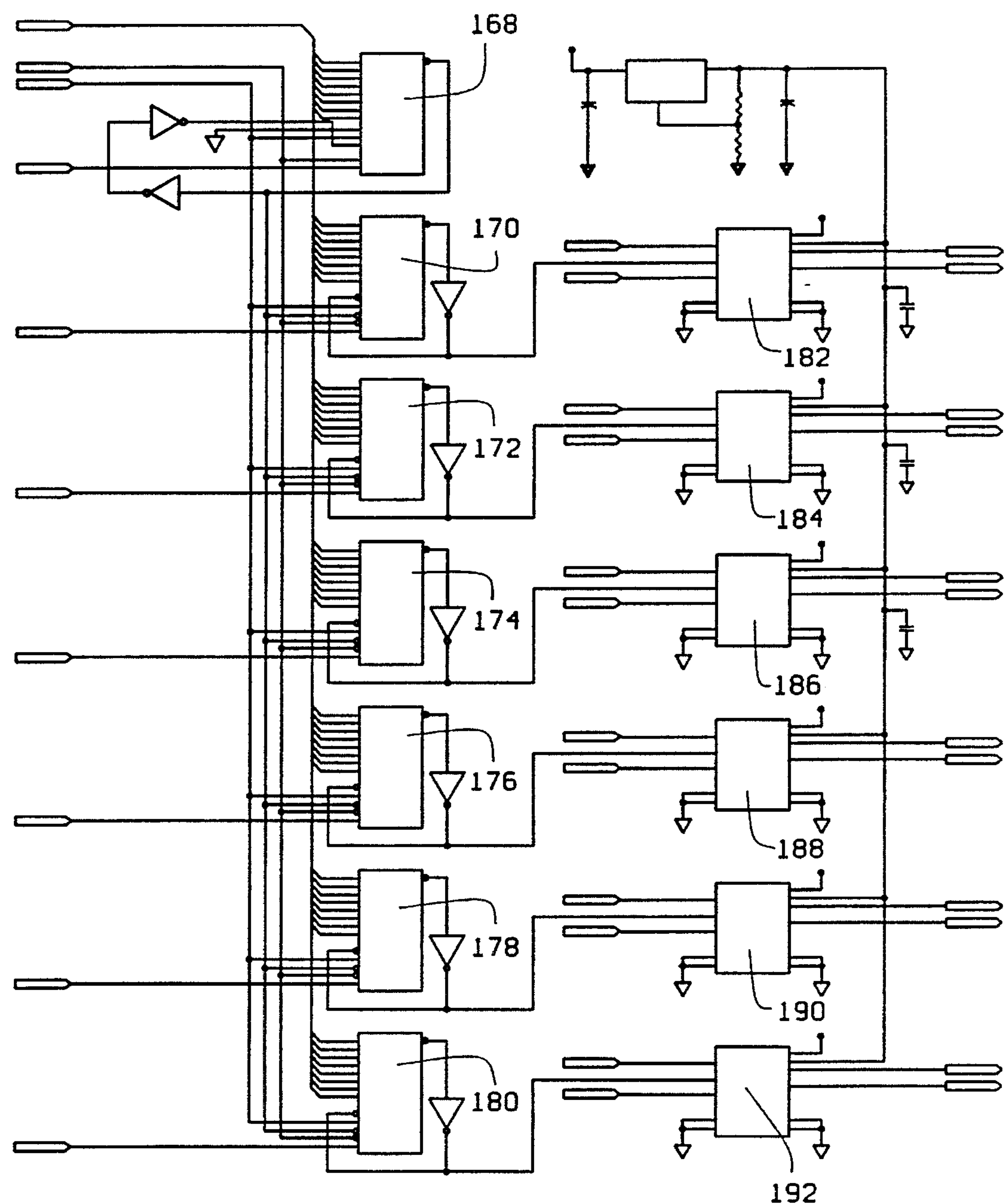
FIG. 12 is an electrical schematic of the motor driver section of the motor controller.
Figure 13A:
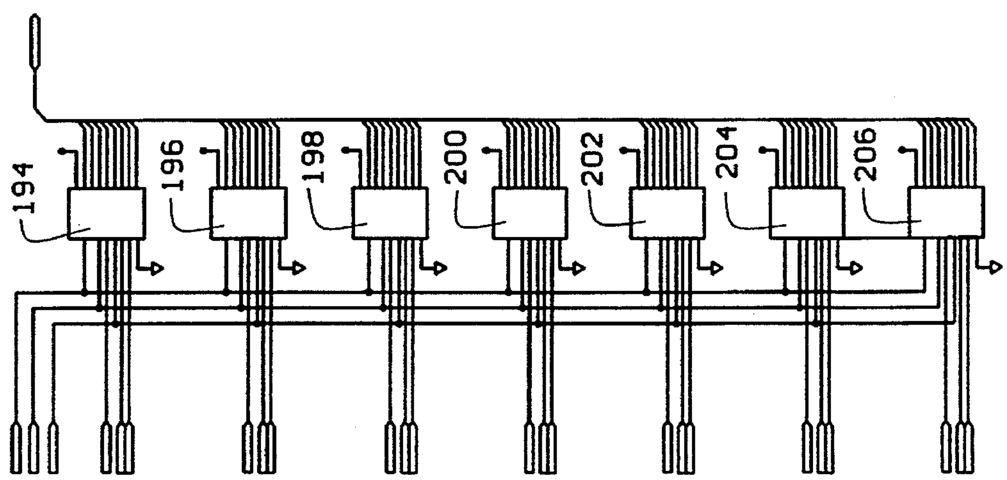
FIGS. 13*a–c* are electrical schematics of the data encoder portion of the motor controller.

As explained above, there are a number of miniaturized dc drive motors for moving various portions of the subjective refractor. The electronics to achieve the controlled movement thereof, including monitoring the data indicative of the position of various optical elements, etc. of the subjective refractor 20 are shown in FIGS. **10–13*c*. Turning first to FIG. 10, an overall block diagram is shown therein detailing the interconnections between the microcontroller unit 140 connected to motor driver circuitry 142 and encoder circuitry 144. The microcontroller unit 140 is shown in greater detail in FIG. 11 and includes a microprocessor 146 connected to a PROM memory 148 and a RAM memory 150 in which are stored the control program, addressing information, operational data, etc. A PAL address decoder 152 and lower order address bit register 154 provide the addressing capability for microprocessor 146. Control registers 156–160 receive and hold motor driver control signals which are written by microprocessor 146. Data buffer 162 is used to prevent overloading of the microprocessor data bus. Address decoders 164 and 166 decode and provide write control signals to counters 168–180 (FIG. 12) which, in turn, provide pulse width modulated enable signals to the six motor drivers 182–192. These drivers are connected to the six DC motors 70, 76, 80 for the trombone and cylinder assemblies on slave plates 42 and 44 contained in the subjective refractor 20. Depicted in FIG. 13 are seven quadrature decoders/counters. Six of those counters, counters 194–204 convert the quadrature signal to position data for each of the six motors 70, 76 and 80 on slave plates 42 and 44 in the subjective refractor 20. The last counter 206 measures the position of the Prince rule for data entry into microprocessor 146**.

Figure 13B:
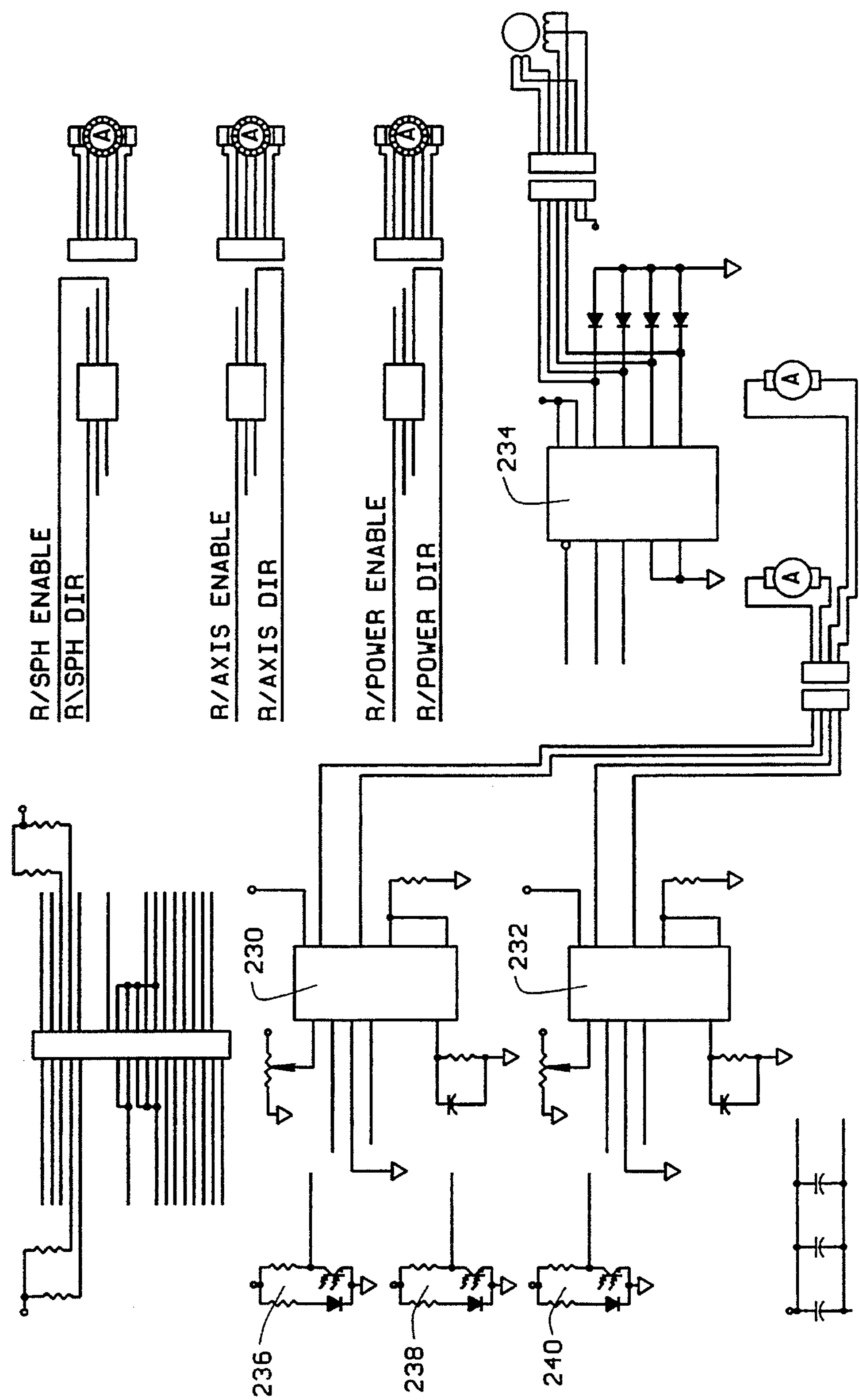

FIG. 13*b* depicts motor connections and driver circuitry associated with the right base plate 42 of the subjective refractor 20. Motor drivers 230 and 232 control the prism and occluder dc motor 90, while motor driver 234 controls the stepper motor 50 used for interpupillary spacing adjustment. Also depicted are a set of optical sensors 236, 238 and 240 which are used to determine an absolute reference point for the trombone and cylinder assemblies, 70, 76 and 80.

Figure 13C:
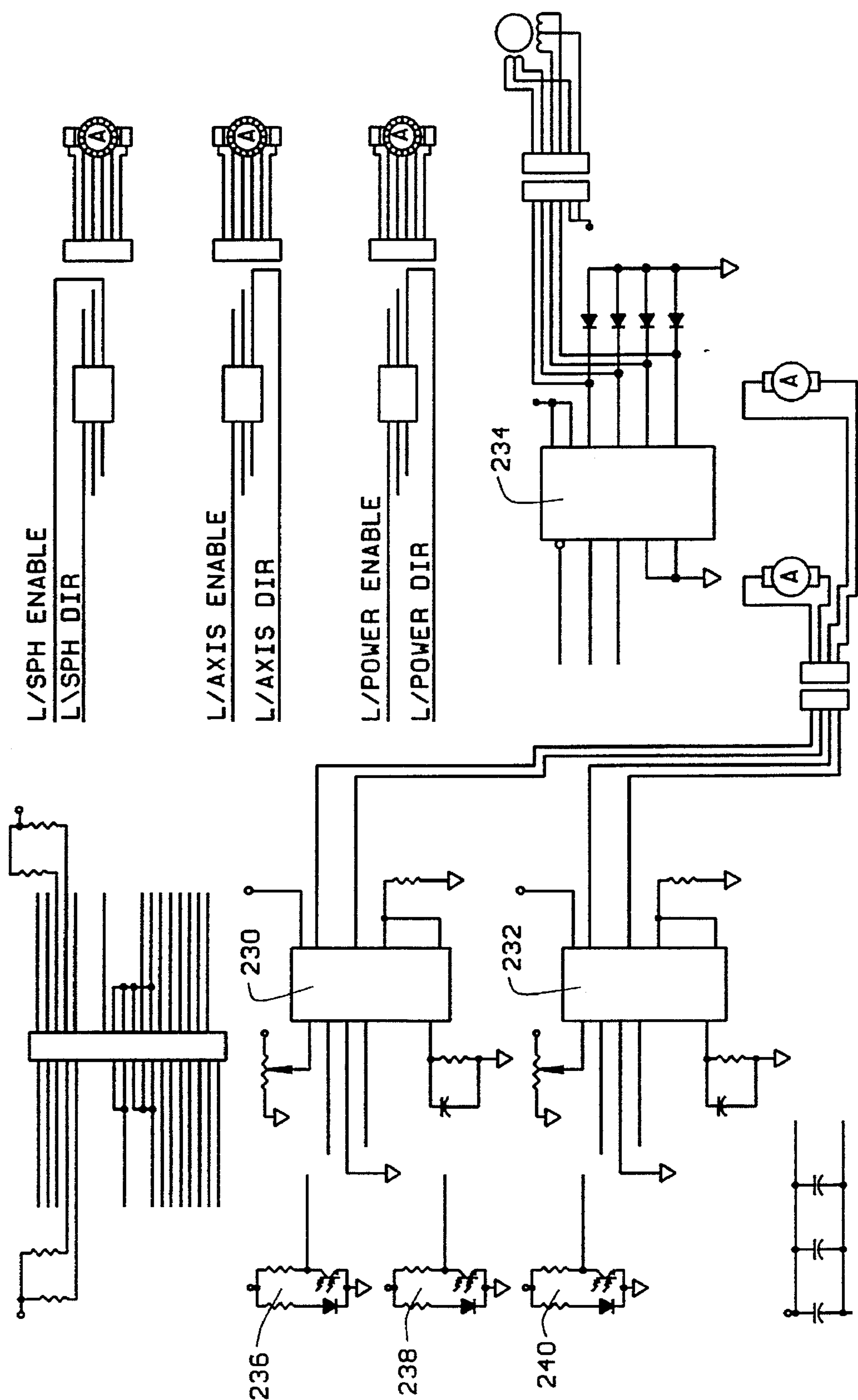

FIG. 13*c* depicts motor connections and driver circuitry associated with the left slave plate 44 of the subjective refractor 20. It is functionally identical to FIG. 13*b*.

Figure 14:
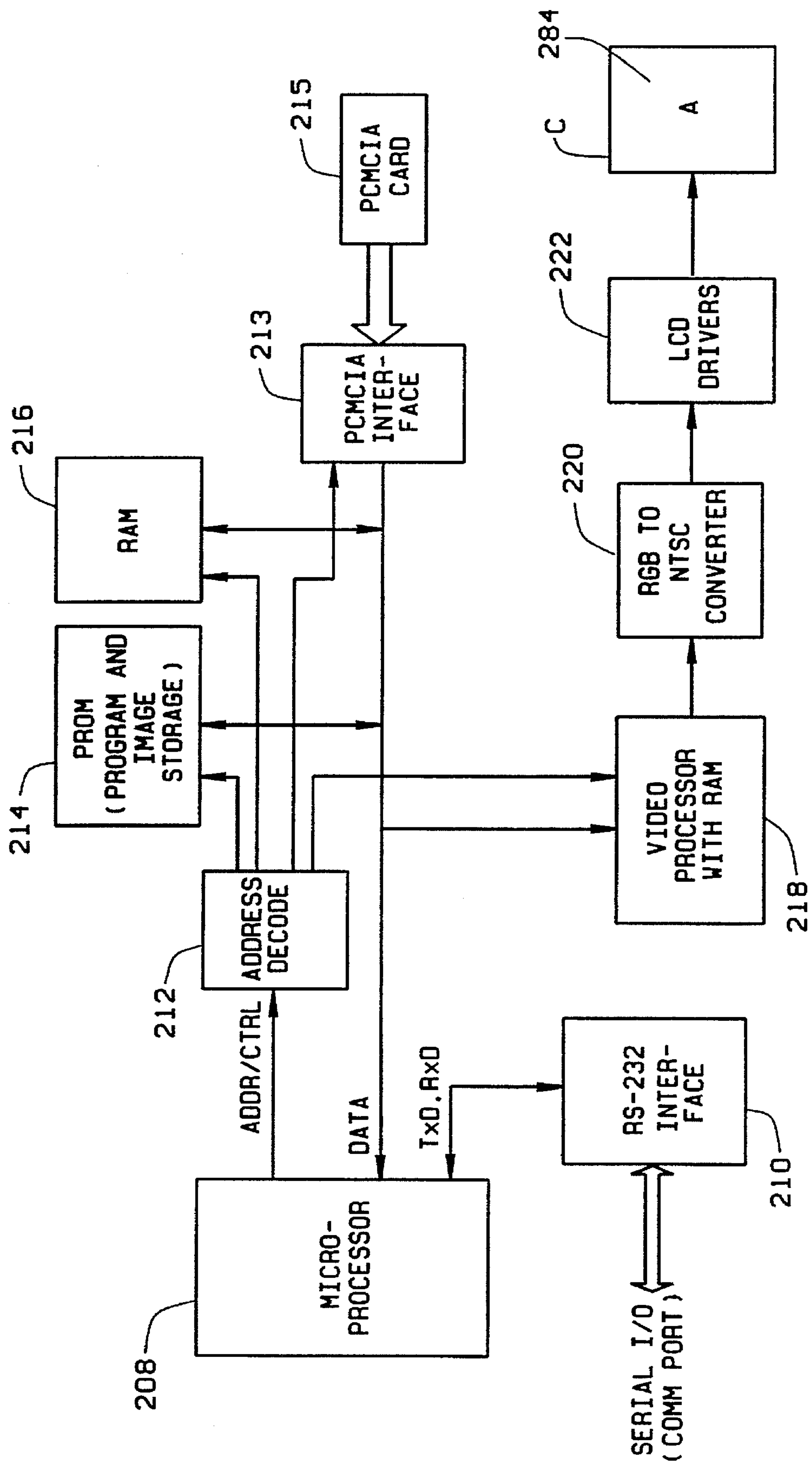
FIG. 14 is a block diagram of the microprocessor based target projector assembly.

The target projector assembly is shown in FIG. 14 and includes a microprocessor 208 in communication with the other microprocessors through RS232 interface 210. An address decoder 212 facilitates the addressing of data in a PROM memory 214 and a RAM memory 216. PROM 214 includes the control program and targets comprised of eye charts for display. A video processor with RAM 218 is driven by the microprocessor 208, and in turn drives an RGB (Red-Green-Blue) to NTSC (National Television Systems Committee) converter 220 to generate control signals for LCD drivers 222 which, in turn, illuminate the LCD display C for generating the projected image 284.

Additional memory, programs, displays, and other data or software may be conveniently input to microprocessor 208 through interface 213 by insertion of a PCMCIA card in card reader slot 215. This provides for convenient system upgrade, configuration changes, and implementation of other functionality with the same hardware configuration. The card reader 215 could be used with any of the microprocessors included in the instrument.

Flow charts for the control programs for each of microprocessors 102, 146, and 208 are attached hereto as Exhibit A. These flow charts describe the functional operation of each of these control programs to facilitate the operation of the subjective refractor 20.

Figure 16:
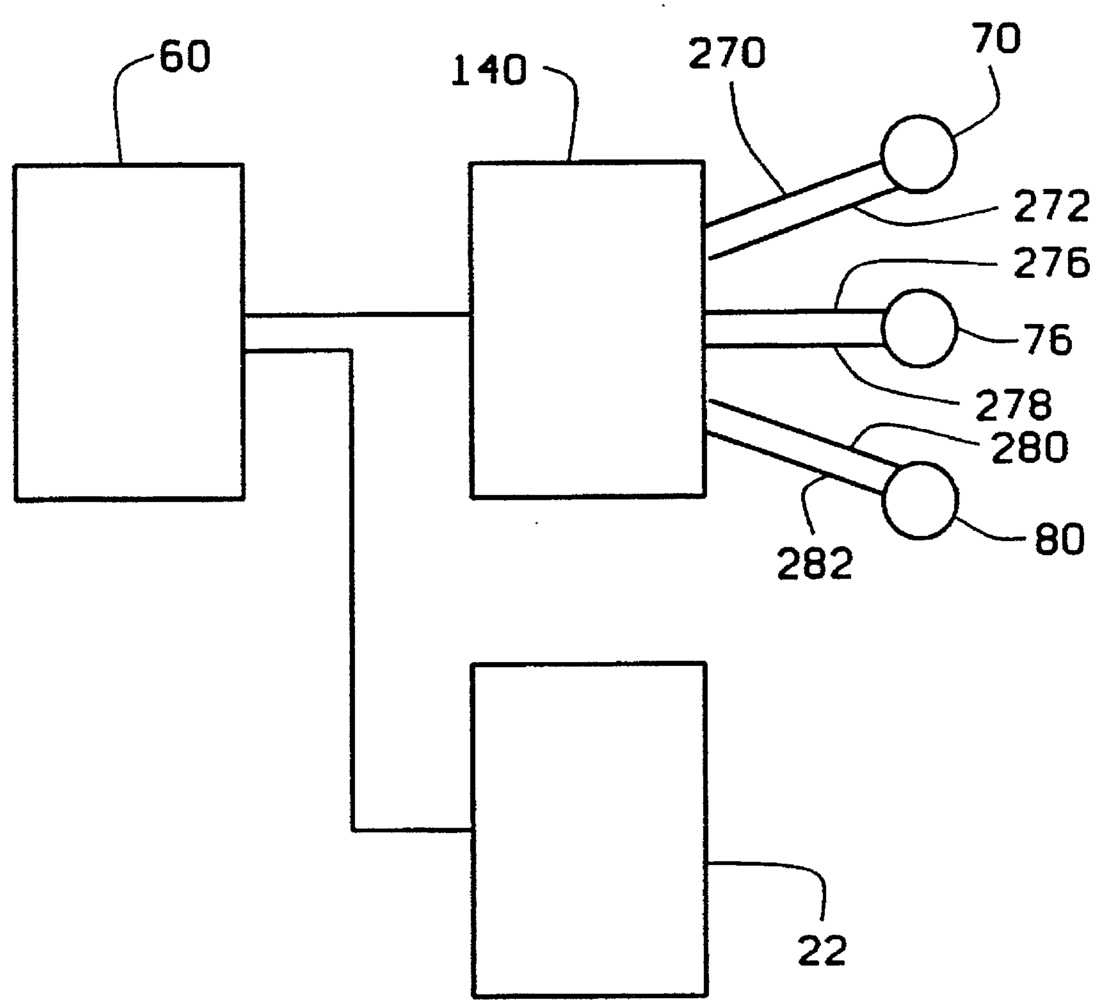
FIG. 16 is a simplified schematic block diagram showing some of the interconnections of components in an embodiment of the invention.

FIG. 16 shows a plurality of motors 70, 76, and 80 for moving some of the optical elements electrically coupled to (as indicated by 270, 276, and 280, respectively) and controlled by motor controller 140, which is connected to remote control 60. The projection unit 22 is also connected to remote control 60. The feedback connections between the motor controller 140 and the motors 70, 76, and 80 are shown at 272, 278, and 282, respectively.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A subjective refractor for determining refractive corrections for each of the patient's eyes, said subjective refractor comprising:

(a) a plurality of optical elements contained in an enclosure, said enclosure being adapted for positioning entirely above the patient's eye level, said optical elements including a beam splitter extending downwardly from said enclosure and adapted for positioning in the patient's line of sight through which the patient may view his surroundings as said subjective refractor is used;

(b) a movable near vision mirror contained in the enclosure for each of the patient's eyes for reflecting light off a near vision testing object and through at least one of said optical elements into the patient's eyes;

(c) distance measuring means extending externally from the enclosure for determining a distance between the near vision testing object and the patient's eyes;

(d) a target projector for projecting a target through said plurality of optical elements and into said patient's eyes, said projector being located in said enclosure;

(e) a plurality of motors for moving at least some of said optical elements;

(f) a motor controller electrically coupled to said motors for monitoring and controlling said motors to thereby adjust positions of said optical elements, said positions corresponding to said refractive corrections; and (g) a control unit electrically coupled to said motor controller for an operator to enter commands to adjust said projected target and said optical element positions in response to the patient's responses.

2. The subjective refractor of claim 1 wherein said target projector projects a selected one of a plurality of standardized eye charts.

3. The subjective refractor of claim 2 wherein said target projector includes a target projecting computer including a display screen, said target projecting computer being responsive to signals from said control unit for selecting one of a plurality of targets for display on said display screen.

4. The subjective refractor of claim 3 wherein said plurality of optical elements includes some elements in a far vision path, other elements in a near vision path, and still other elements in a shared vision path, said plurality of motors including a sight-line changing motor for moving said movable near vision mirror to change a patient's sight line of at least one eye between said far vision path and said near vision path, and vice versa.

5. The subjective refractor of claim 4 wherein said plurality of motors includes an optical element moving motor for moving at least some of said plurality of optical elements into and out of said patient's sight line.

6. The subjective refractor of claim 5 wherein said control unit includes a display for displaying an indication of which of the targets is being projected and an indication of the refractive correction for each of said patient's eyes.

7. The subjective refractor of claim 6 wherein said target projector is positioned solely in said far vision path.

8. The subjective refractor of claim 7 and further comprising a distance encoder to measure the distance to a near vision target.

9. The subjective refractor of claim 4 and further comprising an interpupillary distance adjuster.

10. A subject refractor for determining refractive corrections for each of a patient's eyes at least for far vision distances, said refractor comprising a plurality of optical elements, at least some of which are moveable, a first computer for monitoring and controlling the movement of said moveable optical elements, a second computer including a target projector for projecting a target through said optical elements and into the patient's eyes, and a third computer, said third computer including a plurality of finger controls for an operator to input commands, said third computer being electronically connected with said first and second computer so that said first and second computers carry out said operator commands.

11. The subjective refractor of claim 10 further comprising means for determining a refractive correction for each of a patient's eyes at near vision distances.

12. The subjective refractor of claim 10 wherein at least one of said computers includes a display for displaying an output representative of said refractive correction.

13. The subjective refractor of claim 10 wherein said plurality of optical elements includes some elements in a far vision path, other elements in a near vision path, and still other elements in a shared vision path, and further comprising a plurality of motors for moving said moveable optical elements, said first computer controlling said motors to thereby move selected ones of said moveable optical elements to change a patient's sight line between a far vision path and a near vision path.

14. The subjective refractor of claim 13 and further comprising feedback means between said plurality of motors and said first computer for monitoring the position of those of said moveable optical elements whose movement adjusts the refractive correction of said plurality of optical elements, so that said movement is accurately controlled.

15. The subjective refractor of claim 14 and further comprising an interpupillary distance adjuster.

16. The subjective refractor of claim 15 wherein said target projector is positioned solely in said far vision path and said first computer includes a distance encoder for monitoring the position of a near vision target.

17. The subjective refractor of claim 16 wherein said third computer includes a display for displaying said refractive correction as said subjective refractor is used and an identifier of the target being displayed by said target projector.

18. The subjective refractor of claim 17 wherein said target projector projects a selected one of a plurality of standardized eye charts.

19. The subjective refractor of claim 10 further comprising means for inputting data into at least one of said computers.

20. The subjective refractor of claim 19 wherein said data input means comprises a memory card reader.

21. The subjective refractor of claim 20 wherein said second computer comprises a memory card reader.

* * * * *